US009715998B2

(12) United States Patent
Lu et al.

(10) Patent No.: US 9,715,998 B2
(45) Date of Patent: Jul. 25, 2017

(54) METHOD FOR MONITORING LEVEL OF PARABEN IN COSMETICS

(71) Applicant: KAOHSIUNG MEDICAL UNIVERSITY, Kaohsiung (TW)

(72) Inventors: Chi-Yu Lu, Kaohsiung (TW); Yi-Hsuan Lee, Kaohsiung (TW)

(73) Assignee: Kaohsuing Medical University, Kaohsiung (TW)

( * ) Notice: Subject to any disclaimer, the term of this patent is extended or adjusted under 35 U.S.C. 154(b) by 80 days.

(21) Appl. No.: 14/646,983

(22) PCT Filed: Jan. 9, 2014

(86) PCT No.: PCT/US2014/010798
§ 371 (c)(1),
(2) Date: May 22, 2015

(87) PCT Pub. No.: WO2015/105492
PCT Pub. Date: Jul. 16, 2015

(65) Prior Publication Data

US 2016/0020077 A1 Jan. 21, 2016

(51) Int. Cl.

| | |
|---|---|
| ***G01N 33/15*** | (2006.01) |
| ***G01N 30/72*** | (2006.01) |
| ***H01J 49/26*** | (2006.01) |
| ***H01J 49/40*** | (2006.01) |
| ***H01J 49/00*** | (2006.01) |
| ***H01J 49/16*** | (2006.01) |

(52) U.S. Cl.
CPC ........ *H01J 49/0036* (2013.01); *H01J 49/164* (2013.01)

(58) Field of Classification Search
CPC ............................ H01J 49/0036; H01J 49/164
IPC ........................................ H01J 49/0036,49/164
See application file for complete search history.

(56) References Cited

U.S. PATENT DOCUMENTS

2007/0004045 A1 1/2007 Xu et al.

OTHER PUBLICATIONS

Viglino, Liza, Michèle Prévost, and Sébastien Sauvé. "High throughput analysis of solid-bound endocrine disruptors by LDTD-APCI-MS/MS."Journal of Environmental Monitoring 13.3 (2011): 583-590.*

(Continued)

*Primary Examiner* — Lyle Alexander
*Assistant Examiner* — Robert Eom
(74) *Attorney, Agent, or Firm* — Muncy, Geissler, Olds & Lowe, P.C.

(57) ABSTRACT

The invention discloses a method for monitoring level of paraben comprising: dissolving a sample in a solvent and obtaining a supernatant containing paraben by ultrasonic vibration and high speed centrifugation; performing a derivatization reaction between a derivatization reagent and paraben by adding the derivatization reagent into the supernatant to obtain a derivatization solution containing a tagged paraben; extracting the derivatization solution by an extractant to obtain an extract containing the tagged paraben; and ionizating the tagged paraben by a laser beam and analyzing mass-to-charge ratio of the tagged paraben by an analyzer to determine molecular weight thereof.

7 Claims, 4 Drawing Sheets

(56) References Cited

OTHER PUBLICATIONS

Yu, Yiyi, et al. "Determination of pharmaceuticals, steroid hormones, and endocrine-disrupting personal care products in sewage sludge by ultra-high-performance liquid chromatography—tandem mass spectrometry." Analytical and bioanalytical chemistry 399.2 (2011): 891-902.*
Nordhoff, E., et al. "Matrix-assisted laser desorption/ionization mass spectrometry of nucleic acids with wavelengths in the ultraviolet and infrared." Rapid Communications in Mass Spectrometry 6.12 (1992): 771-776.*
Kuck, "Mass spectrometry and gas-phase ion chemistry of phenols", The chemistry of phenols Part 2, 2003, pp. 324-325.
PerkinElmer Inc, "A Reference Notebook of LC/SQ MS Applications", Flexar SQ 300MS, 2011, pp. 1-57,Second Edition.
Zhang et al., "A Novel Strategy for MALDI-TOF MS Analysis of Small Molecules", J Am Soc Mass Spectrom, 2010, pp. 154-160, vol. 21.
Saraji et al., "Single-drop microextraction followed by in-syringe derivatization and GC-MS detection for the determination of parabens in water and consmetic products", J.Sep.Sci, 2009, pp. 988-995, vol. 32.
Cruces-Blanco et al., "Spectrofluorimetric Determination of Methyl Paraben in Pharmaceutical Preparations by Means of its Dansyl Chloride Derivative", Mikrochim Acta, 2000, pp. 107-111, vol. 134.
Barbas et al, "Separation of Paraben Preservatives by Reversed-Phase HPLC," Agilent Technologies, Inc., 2005, 4 pages.
Chu et al, "A Rapid Method for the Simultaneous Determination of Preservatives in Soy Sauce," Journal of Food and Drug Analysis, 2003, pp. 246-250, vol. 11, No. 3.
Miao et al, "Matrix of 3,4-Diaminobenzophenone for Analysis of Phospholipids by Matrix-Assisted Laser Desorption/Ionization-Time of Flight-Mass Spectrometry," Chinese Journal of Analytical Chemistry, 2011, p. 605-610, vol. 39.
Samburova et al, Characterization of high molecular weight compounds in urban atmospheric particles, Atmos. Chem. Phys., 2005, pp. 2163-2170, vol. 5.
Shanmugam et al, "GC-MS method for the determination of paraben preservatives in the human breast," Microchemical Journal, 2010, pp. 391-396, vol. 96.
Yu et al, "Determination of pharmaceuticals, steroid hormones, and endocrine-disrupting personal care products in sewage sludge by ultra-high-performance liquid chromatography-tandem mass spectrometry," Anal. Bioanal. Chem., 2011, pp. 891-902, vol. 399, Published Online: Oct. 28, 2010.

* cited by examiner

METHOD FOR MONITORING LEVEL OF PARABEN IN COSMETICS

BACKGROUND OF THE INVENTION

1. Field of the Invention

The present invention generally relates to a method for monitoring paraben and, more particularly, to a method for monitoring level of paraben.

2. Description of the Related Art

With respect to FIG. 1, parabens, also named as para-hydroxybenzoic acid, are a class of chemicals including methyparaben (MP), ethylparaben (EP), propylparaben (PP), butylparaben (BP), isopropylparaben (IPP), isobutyl-paraben (IBP) and secbutylparaben (SBP). With bactericidal and fungicidal properties, parabens are widely used as preservative by cosmetic and pharmaceutical industries to prolong shelf life of cosmetics and medications. However, parabens are becoming increasingly controversial. As a xenoestrogen (XE) and an endocrine-disrupting compound (EDC, also called as environmental hormone), parabens pose estrogenic activity and may affect male reproductive system, thereby being harmful to human body. Moreover, for human body with irritable the physique, parabens may probably induce allergic reaction and photosensitivity. Therefore, it is necessary to highly monitor the level of paraben.

In a conventional method for monitoring level of paraben, first by a process named solid phase extraction, a membrane or a column is used to extract a sample. The resultant extract is further analyzed by reversed-phase high performance liquid chromatography (RP-HPLC) in combination with ultraviolet detector (UV) or diode array detector (DAD).

However, due to the process of solid phase extraction comprises separation and extraction, 0.2 to 20 g of the sample is needed in the conventional method for monitoring level of paraben. That is, the conventional method for monitoring level of paraben is not suitable for the samples, which are expensive or difficult to afford.

Furthermore, due to the RP-HPLC procedure, the conventional method for monitoring level of paraben requires a long analyzing time for one sample and an additional cleaning time for cleaning the column between one and another samples used in the RP-HPLC procedure. That's why the conventional method for monitoring level of paraben is time-cost and not suitable for large-scale screening.

Besides the cleaning time, a lot of organic solvents are also required to clean the column used in the RP-HPLC procedure. The resultant waste organic solvents are therefore becoming pollution to the environment. Thus, the conventional analysis of paraben may be harmful to the environment.

In light of this, it is necessary to improve the conventional method for monitoring level of paraben.

SUMMARY OF THE INVENTION

It is therefore the objective of this invention to provide a method for monitoring level of paraben with improved accuracy, decreasing amount of the samples required in the method.

It is another objective of this invention to provide a method for monitoring level of paraben, significantly decreasing time required for the method and being suitable for large-scale screening.

It is yet another objective of this invention to provide a method for monitoring level of paraben with a decreased quantity of waste organic solvents, preventing from environmental pollution.

One embodiment of the invention discloses a method for monitoring level of paraben comprising: dissolving a sample in a solvent and obtaining a supernatant containing paraben by ultrasonic vibration and high speed centrifugation; performing a derivatization reaction between a derivatization reagent and paraben by adding the derivatization reagent into the supernatant to obtain a derivatization solution containing a tagged paraben; extracting the derivatization solution by an extractant to obtain an extract containing the tagged paraben; and ionizating the tagged paraben by a laser beam and analyzing mass-to-charge ratio of the tagged paraben by an analyzer to determine molecular weight thereof.

In a preferred form shown, the method for monitoring level of paraben further comprises adjusting temperature of the supernatant containing paraben to 30-80° C. prior to adding the derivatization reagent into the supernatant.

In a preferred form shown, the derivatization reagent has a sulfonyl chloride group whereon the derivatization reaction is performed with a hydroxyl group of paraben. Preferably, the derivatization reagent is selected from 1,3-benzothiazole-6-sulfonyl chloride, 4-dimethylaminoazobenzene-4'-sulfonyl chloride or dansyl chloride.

In a preferred form shown, the laser beam has a wavelength of 330 to 360 nm.

In a preferred form shown, the sample is in a form of solution, lotion, emulsion, cream or gel.

In a preferred form shown, the method for monitoring level of paraben further comprises adding an internal standard into the supernatant and performing the derivatization reaction between the derivatization reagent and the internal standard. Preferably, the internal standard is an isotope of paraben.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
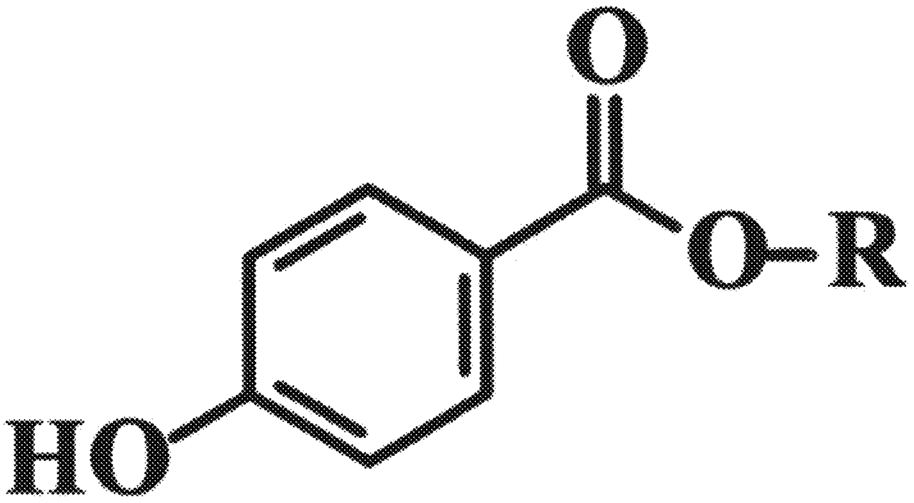
FIG. 1 depicts the general chemical structure of a paraben.
Figure 2:
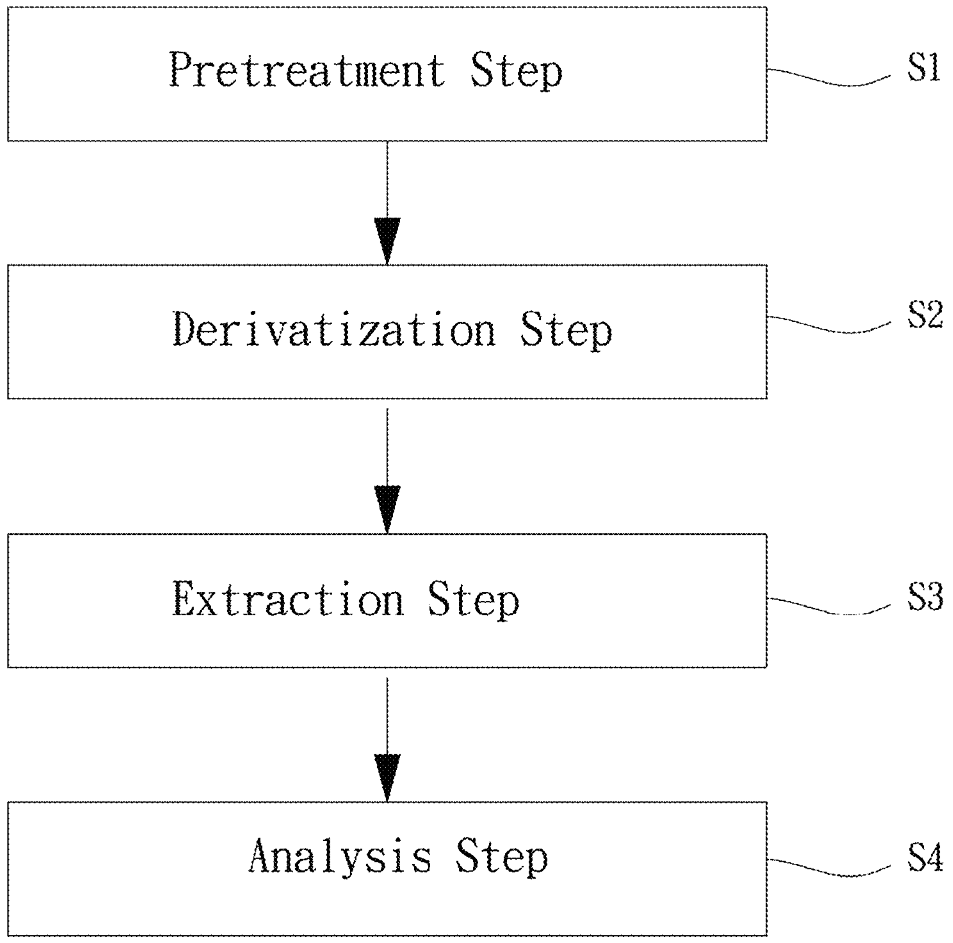
FIG. 2 depicts a flow chart of the first embodiment of the invention.

In the various figures of the drawings, the same numerals designate the same or similar parts. Furthermore, when the term "first", "second", "third", "fourth", "inner", "outer" "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

A method for monitoring level of paraben according to preferred teachings of the invention comprises: a pretreatment step "S1", a derivatization step "S2", an extraction step "S3" and an analysis step "S4".

In the pretreatment step "S1", a sample is dissolved in a solvent, followed by ultrasonic vibration and high-speed centrifugation to obtain a supernatant. The supernatant contains paraben. In the derivatization step "S2", a derivatization reagent is added into the supernatant. A derivatization reaction can occur between the derivatization reagent and paraben, thereby forming a tagged paraben in a derivatization solution. In the extraction step "S3", the derivatization solution is extracted by an extractant to obtain an extract containing the tagged paraben. And in the analysis step "S4", the tagged paraben is ionized by a laser beam to form a vaporized ion. Mass-to-charge ratio of the vaporized ion is further analyzed to determine a molecular weight of the vaporized ion thereof.

In detail, in the pretreatment step "S1", the sample can be easily available cosmetics or medications, such as cosmetics in a form of solution, lotion, emulsion, cream or gel or medications in a form of pill, capsule, powder, solution, pastil, gel or cream. The amounts of the sample is between 0.1 and 100 mg. The solvent can be selected from organic solvents as acetonitrile, acetone or methanol. Alternatively, the solvent can be a mixture in an appropriate portion of the organic solvents. In the preferable embodiment, 100 mg of the sample is dissolved in 1 mL of acetonitrile.

After dissolving the sample in the solvent, ultrasonic vibration can be performed to improve solubility of paraben. Time of ultrasonic vibration can set forth in 1 to 30 minutes. Next, high-speed centrifugation can be carried out to remove impurities. Preferably, high-speed centrifugation can be carried out as 10000 to 13000 rpm for 1 to 30 minutes. In the preferable embodiment, the sample is dissolved in the solvent, followed by ultrasonic vibration for 10 minutes and high-speed centrifugation at 13000 rpm for 10 minutes to obtain the supernatant containing paraben.

Figure 3:
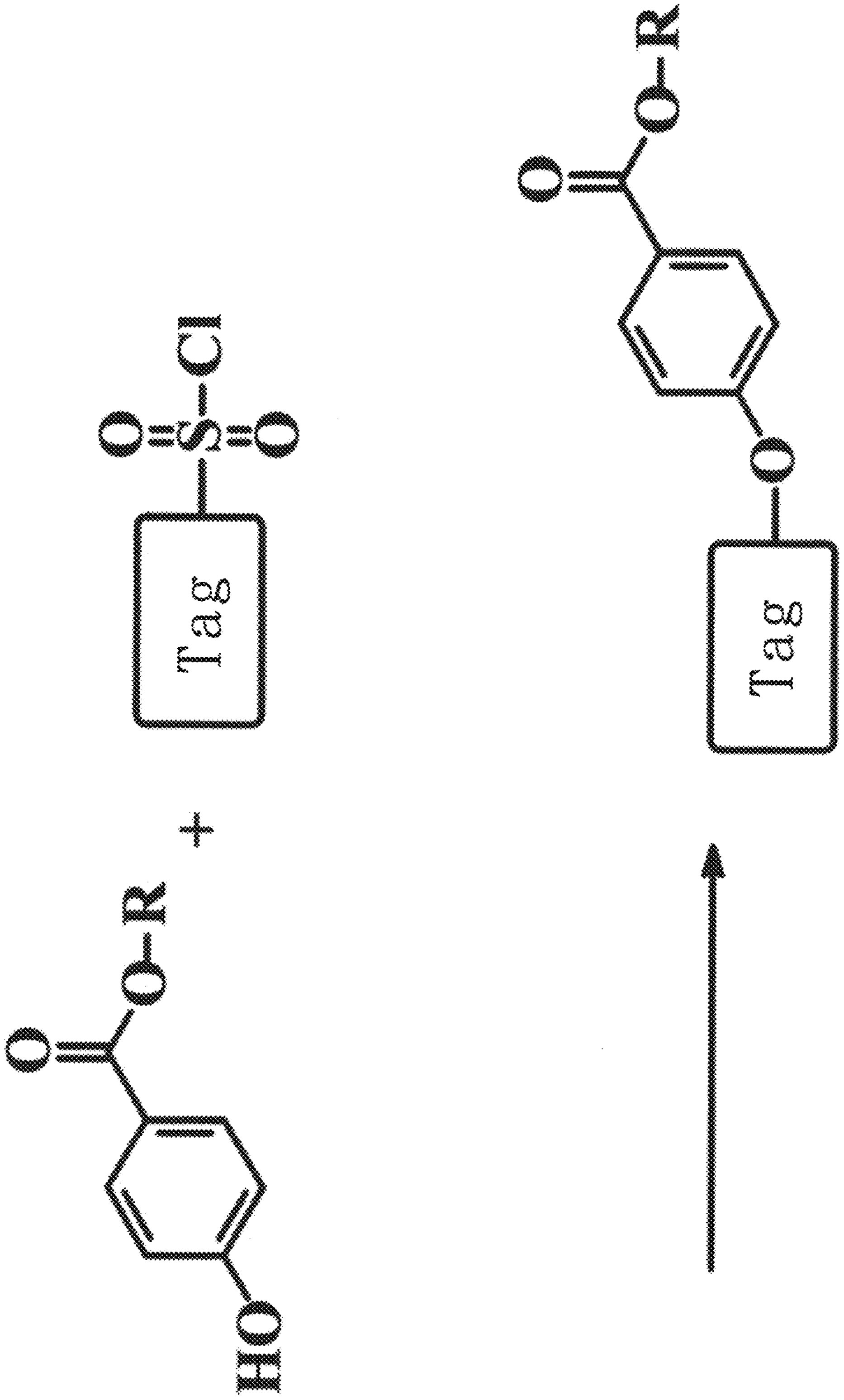
FIG. 3 depicts the chemical equation of the derivatization reaction.

In the derivatization step "S2", the derivatization reagent is added into the supernatant, with the derivatization reaction is performed between the derivatization reagent and paraben. Preferably, the derivatization reagent has a strong absorbance at wavelength of 330 to 360 nm. The derivatization reagent has a sulfonyl chloride group (—$SO_2Cl$) whereon the derivatization reaction is performed with a hydroxyl group of paraben. Therefore, the derivatization solution containing the tagged paraben is obtained, as shown in FIG. 3. The derivatization reagent can be selected from, but not limited to, 1,3-benzothiazole-6-sulfonyl chloride, 4-dimethylaminoazobenzene-4'-sulfonyl chloride (also named as dabsyl chloride) or dansyl chloride.

Figure 4:
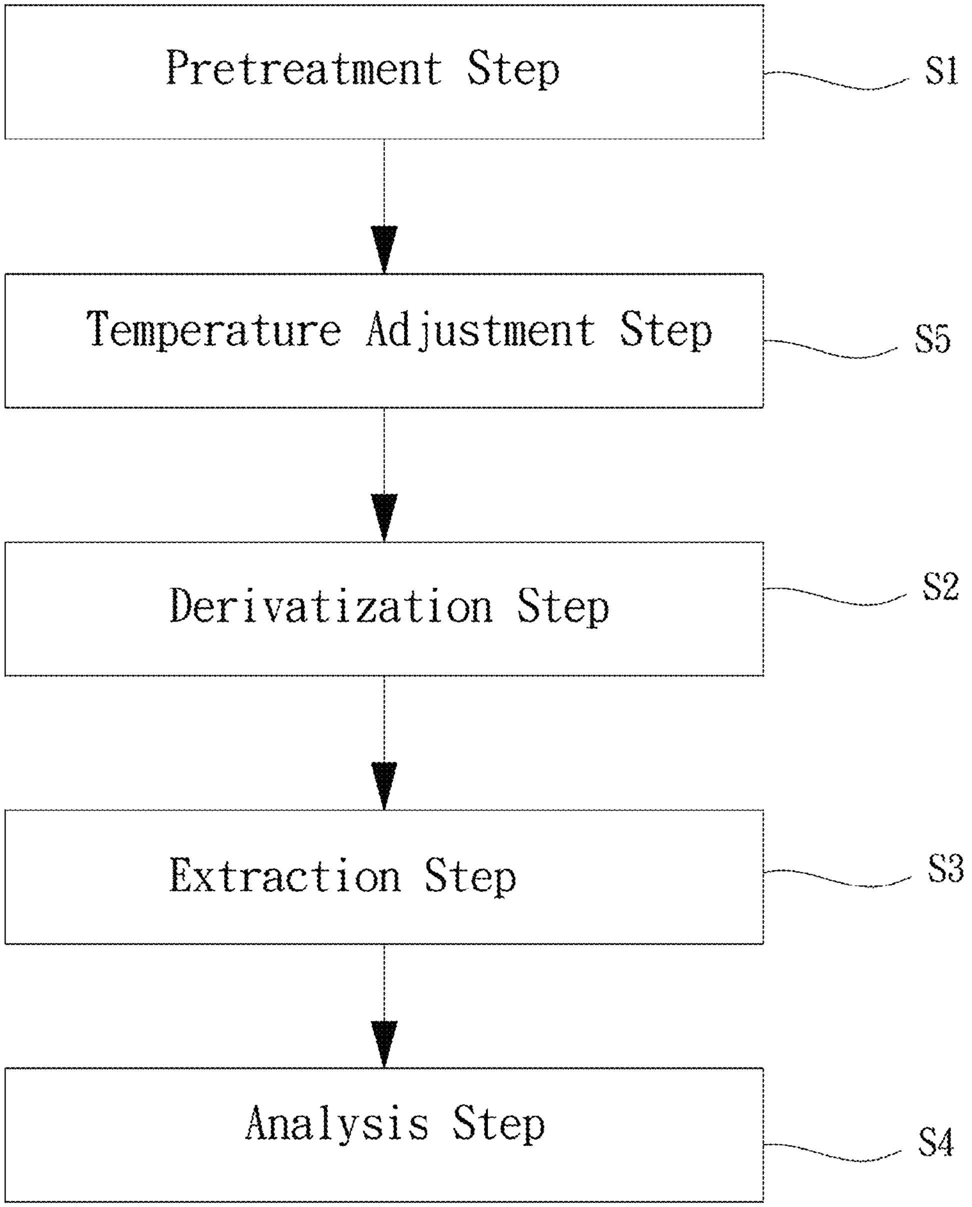
FIG. 4 depicts a flow chart of the second embodiment of the invention.

Moreover, according to the derivatization reagent used, pH value of the supernatant can be adjusted to allow the performance of the derivatization reaction. In the preferable embodiment, the derivatization reagent is chosen to be dansyl chloride. The pH value of the supernatant should be adjusted to pH 8 to 10 by using an alkali, such as sodium carbonate or sodium bicarbonate. With reference to FIG. 4, a temperature adjustment step "S5" can be further perform between the pretreatment step "S1" and the derivatization step "S2", by adjusting the temperature of the supernatant as 30 to 80° C. the derivatization reaction is accelerated.

In the preferably embodiment, 5 μL of the supernatant is pH-adjusted by 10 μL of sodium bicarbonate (10 to 500 mM, adjustment to pH 8 to 10), followed by adding 10 μL of dansyl chloride (dissolved in acetone with a concentration of 0.25 to 2 mg/mL) to obtain a mixture. The mixture is heated to 30 to 80° C. to accelerate the derivatization reaction. That is, the derivatization reaction is performed between the sulfonyl chloride group of the derivatization reaction and the hydroxyl group of paraben for 5 to 30 minutes, thereby forming the tagged paraben in the resultant derivatization solution.

In the extraction step "S3", the extract containing the tagged paraben is obtained by using the extractant. Preferably, the extractant can be organic solvents as hexyl acetate, hexane, tolune or ethyl acetate with an amount of 10 to 50 μL. In the preferable embodiment, the extraction step "S3" is performed with 20 μL of ethyl acetate and the tagged paraben will dissolve in ethyl acetate, thereby obtaining the extract.

Preferably, MALDI-TOF MS (matrix-assisted lased desorption/ionization-time of flight mass spectrometer) is used in the analysis step "S4". In detail, the extract can be spotted onto a target plate of the MALDI-TOF MS, followed by covering with a matrix. The extract and the matrix can be co-crystallized for the following process. The matrix is preferably chosen from substances with a strong absorbance at 330 to 360 nm. For example, α-cyanol-4-hydroxycinnamic acid (CHCA), 3,5-dimethoxy-4-hydroxycinnamic acid (sinapinic acid, SA) or 2,5-dihydroxybenzoic acid (2,5-DHB). In the preferable embodiment, the matrix is CHCA (0.5 μL, 10 mg/mL).

The laser beam with wavelength of 330 to 360 nm is fired at the co-crystallized extract-matrix mixture, assisting the ionization of the co-crystallized extract-matrix mixture and forming a vaporized ion. The vaporized ion is further accelerated by an electric field and enters into an analyzer to determine the mass-to-charge ratio (m/z) of the vaporized ion. The analyzer can be a time-of-flight analyzer (TOF analyzer), quadrupole analyzer, ion trap analyzer (IT analyzer) or Fourier transform-ion cyclotron resonance (FT-ICR). In the preferable embodiment, the analyzer is TOF analyzer with advantage of rapid analysis.

Preferably, an internal standard can be further added into the supernatant in the derivatization step "S2". The internal standard can be an isotope of paraben. In the preferably embodiment, ethyl-d5 paraben (16 μg/mL) is used as the internal standard. The internal standard also can be derivatizated by the derivatization reagent, co-crystallized with the matrix and ionized by the laser beam. Level of paraben in the sample can be calculated according to the peak area of the internal standard and the peak area of the sample.

In order to evaluate the preferable embodiment of the invention can be used for monitoring level of paraben in the sample, several commercially available cosmetics in form of solution, gel, lotion, cream and mask, and commercially available liquid medication is used as the sample. By the preferable embodiment of the invention, level of paraben in the samples mentioned above is monitored and the results are shown in Table 1 to 6, wherein MP shows methylparaben, EP shows ethylparaben, PP shows propylparaben, and BP shows butylparaben.

TABLE 1

| Level of paraben of commercially available cosmetics in form of solution | | | | | | | | | | | | | |
|---|---|---|---|---|---|---|---|---|---|---|---|---|---|
| | Concentration (μg/mL) | | | | Relative Standard Deviation (%) | | | | Weight Percentage of Sample (%) | | | | |
| # | MP | EP | PP | BP | MP | EP | PP | BP | MP | EP | PP | BP | Sum |
| 1 | 36.53 ± 0.001 | — | — | — | 2.43 | — | — | — | 0.04 | — | — | — | 0.04 |
| 2 | 53.19 ± 0.03 | 12.78 ± 0.002 | — | — | 3.40 | 9.85 | — | — | 0.05 | 0.01 | — | — | 0.07 |
| 3 | 113.25 ± 0.04 | 33.41 ± 0.002 | — | — | 2.15 | 2.62 | — | — | 0.11 | 0.03 | — | — | 0.15 |
| 4 | 67.19 ± 0.07 | 27.77 ± 0.004 | — | — | 6.40 | 10.24 | — | — | 0.07 | 0.03 | — | — | 0.09 |
| 5 | 63.11 ± 0.03 | — | 2.27 ± 0.001 | — | 2.86 | — | 5.23 | — | 0.06 | — | 0.002 | — | 0.07 |

With reference to Table 1, the samples #1 to #5 are commercially available cosmetics in form of solution. 100 mg of the samples are analyzed by the preferably embodiment of the invention and levels of paraben, including methylparaben, ethylparaben, propylparaben, and butylparaben, are recorded in Table 1. The results show that the samples #1 to #5 contain 0.04 to 0.15% of paraben, respectively. Accordingly, the preferably embodiment of the invention is suitable for monitoring level of paraben when the samples are merely 100 mg.

TABLE 2

| Level of paraben of commercially available cosmetics in form of gel | | | | | | | | | | | | | |
|---|---|---|---|---|---|---|---|---|---|---|---|---|---|
| | Concentration (μg/mL) | | | | Relative Standard Deviation (%) | | | | Weight Percentage of Sample (%) | | | | |
| # | MP | EP | PP | BP | MP | EP | PP | BP | MP | EP | PP | BP | Sum |
| 6 | 119.79 ± 1.210 | — | — | — | 6.4 | — | — | — | 0.12 | — | — | — | 0.12 |
| 7 | 49.27 ± 0.320 | 1.14 ± 0.010 | — | — | 4.05 | 7.22 | — | — | 0.049 | 0.0011 | — | — | 0.05 |

With reference to Table 2, the samples #6 and #7 are commercially available cosmetics in form of gel. 100 mg of the samples are analyzed by the preferably embodiment of the invention and levels of paraben are recorded in Table 2. The results show that the samples #6 and #7 contain 0.05 to 0.12% of paraben, respectively.

TABLE 3

| Level of paraben of commercially available cosmetics in form of lotion or emulsion | | | | | | | | | | | | | |
|---|---|---|---|---|---|---|---|---|---|---|---|---|---|
| | Concentration (μg/mL) | | | | Relative Standard Deviation (%) | | | | Weight Percentage of Sample (%) | | | | |
| # | MP | EP | PP | BP | MP | EP | PP | BP | MP | EP | PP | BP | Sum |
| 8 | 44.96 ± 0.002 | 6.51 ± 0.0002 | 32.32 ± 0.003 | 0.12 ± 0.0004 | 3.53 | 3.16 | 7.91 | 7.72 | 0.04 | 0.01 | 0.03 | 0.00 | 0.08 |
| 9 | 87.7 ± 0.003 | 11.99 ± 0.010 | 5.24 ± 0.001 | 17.76 ± 0.005 | 2.06 | 3.57 | 2.12 | 2.41 | 0.09 | 0.01 | 0.01 | 0.02 | 0.12 |
| 10 | 36.51 ± 0.010 | 1.63 ± 0.001 | 32.84 ± 0.020 | — | 1.32 | 5.63 | 4.13 | — | 0.04 | 0.002 | 0.03 | — | 0.07 |
| 11 | 17.84 ± 0.003 | 5.32 ± 0.005 | 2.46 ± 0.002 | 8.44 ± 0.010 | 1.24 | 5.39 | 8.13 | 10.15 | 0.02 | 0.01 | 0.00 | 0.01 | 0.03 |
| 12 | 96.83 ± 0.050 | 1.39 ± 0.002 | 1.13 ± 0.001 | — | 2.29 | 11.97 | 12.41 | — | 0.10 | 0.001 | 0.001 | — | 0.10 |

With reference to Table 3, the samples #8 and #12 are commercially available cosmetics in form of lotion or emulsion. 100 mg of the samples are analyzed by the preferably embodiment of the invention and levels of paraben are recorded in Table 3. The results show that the samples #8 to #12 contain 0.03 to 0.12% of paraben, respectively.

TABLE 4

Level of paraben of commercially available cosmetics in form of cream

| # | Concentration (μg/mL) | | | | Relative Standard Deviation (%) | | | | Weight Percentage of Sample (%) | | | | |
|---|---|---|---|---|---|---|---|---|---|---|---|---|---|
| | MP | EP | PP | BP | MP | EP | PP | BP | MP | EP | PP | BP | Sum |
| 13 | 1.02 ± 0.001 | 99.95 ± 0.03 | 55.49 ± 0.02 | — | 8.4 | 1.95 | 2.56 | — | 0.001 | 0.10 | 0.06 | — | 0.16 |
| 14 | 64.28 ± 0.003 | 7.76 ± 0.004 | 14.39 ± 0.001 | 37.62 ± 0.001 | 3.62 | 7.61 | 9.62 | 3.09 | 0.06 | 0.01 | 0.01 | 0.04 | 0.12 |
| 15 | 42.61 ± 0.02 | 11.11 ± 0.01 | 4.97 ± 0.004 | 30.21 ± 0.02 | 2.67 | 5.32 | 7.67 | 6.70 | 0.04 | 0.01 | 0.005 | 0.03 | 0.09 |
| 16 | 87.7 ± 0.003 | 11.99 ± 0.01 | 5.24 ± 0.001 | 17.76 ± 0.005 | 2.06 | 3.57 | 2.12 | 2.41 | 0.09 | 0.01 | 0.01 | 0.02 | 0.12 |
| 17 | 36.51 ± 0.01 | 1.63 ± 0.001 | 32.84 ± 0.02 | — | 1.32 | 5.63 | 4.13 | — | 0.04 | 0.002 | 0.03 | — | 0.07 |

With reference to Table 4, the samples #13 to #17 are commercially available cosmetics in form of cream. 100 mg of the samples are analyzed by the preferably embodiment of the invention and levels of paraben are recorded in Table 4. The results show that the samples #13 to #17 contain 0.07 to 0.16% of paraben, respectively.

TABLE 5

Level of paraben of commercially available cosmetics in form of mask

| # | Concentration (μg/mL) | | | | Relative Standard Deviation (%) | | | | Weight Percentage of Sample (%) | | | | |
|---|---|---|---|---|---|---|---|---|---|---|---|---|---|
| | MP | EP | PP | BP | MP | EP | PP | BP | MP | EP | PP | BP | Sum |
| 18 | 51.90 ± 0.02 | 2.15 ± 0.001 | 1.11 ± 0.001 | — | 2.08 | 3.63 | 13.24 | — | 0.05 | 0.002 | 0.001 | — | 0.06 |
| 19 | 43.58 ± 0.04 | 4.49 ± 0.001 | — | — | 5.90 | 1.13 | — | — | 0.04 | 0.004 | — | — | 0.05 |
| 20 | 33.61 ± 0.02 | 1.61 ± 0.002 | — | — | 4.55 | 9.67 | — | — | 0.03 | 0.002 | — | — | 0.04 |
| 21 | 61.52 ± 0.03 | — | — | — | 2.96 | — | — | — | 0.06 | — | — | — | 0.06 |
| 22 | 14.63 ± 0.02 | — | — | — | 8.46 | — | — | — | 0.01 | — | — | — | 0.01 |

With reference to Table 5, the samples #18 to #22 are commercially available cosmetics in form of mask. 100 mg of the samples (only essence of the mask is used) are analyzed by the preferably embodiment of the invention and levels of paraben are recorded in Table 5. The results show that the samples #18 to #22 contain 0.01 to 0.06% of paraben, respectively.

TABLE 6

Level of paraben of commercially available liquid medication

| # | Concentration (μg/mL) | | | | Relative Standard Deviation (%) | | | | Weight Percentage of Sample (%) | | | | |
|---|---|---|---|---|---|---|---|---|---|---|---|---|---|
| | MP | EP | PP | BP | MP | EP | PP | BP | MP | EP | PP | BP | Sum |
| 23 | 39.76 ± 0.02 | — | — | — | 3.00 | — | — | — | 0.04 | — | — | — | 0.04 |
| 24 | 225.55 ± 0.03 | — | — | — | 7.60 | — | — | — | 0.23 | — | — | — | 0.23 |
| 25 | 39.69 ± 0.01 | — | — | — | 1.54 | — | — | — | 0.04 | — | — | — | 0.04 |
| 26 | 48.69 ± 0.01 | — | — | — | 1.33 | — | — | — | 0.05 | — | — | — | 0.05 |
| 27 | 10.07 ± 0.01 | — | 3.30 ± 0.002 | — | 3.82 | — | 4.34 | — | 0.01 | — | 0.003 | — | 0.01 |

With reference to Table 6, the samples #23 to #27 are commercially available liquid medication. 100 mg of the samples are analyzed by the preferably embodiment of the invention and levels of paraben are recorded in Table 6. The results show that the samples #23 to #27 contain 0.01 to 0.23% of paraben, respectively.

Moreover, one of the commercially available cosmetics in form of solution, gel, lotion and cream and one of the commercially available liquid medications are used as the samples. That is, one of the samples #1 to #5, one of the samples #6 and #7, one of the samples #8 to #12, one of the samples #13 to #17, one of the samples #18 to #22 and one of the samples #23 to #27 are used as the samples #28 to #33. 0.1 mg of the samples are analyzed by the preferably embodiment of the invention and levels of paraben are recorded in Table 7.

TABLE 7

Level of paraben of commercially available samples

| No. | Concentration (μg/mL) MP | EP | PP | BP | Relative Standard Deviation (%) MP | EP | PP | BP | Weight Percentage of Sample (%) MP | EP | PP | BP | Sum |
|---|---|---|---|---|---|---|---|---|---|---|---|---|---|
| 28 | 12.86 ± 0.260 | — | — | — | 12.93 | — | — | — | 0.13 | — | — | — | 0.13 |
| 29 | 60.38 ± 0.720 | — | — | — | 7.55 | — | — | — | 0.60 | — | — | — | 0.60 |
| 30 | 25.82 ± 0.490 | — | — | — | 11.98 | — | — | — | 0.26 | — | — | — | 0.26 |
| 31 | 27.44 ± 0.220 | — | — | — | 4.97 | — | — | — | 0.27 | — | — | — | 0.27 |
| 32 | 143.6 ± 2.220 | 35.68 ± 0.360 | 11.06 ± 0.220 | 29.87 ± 1.180 | 9.77 | 6.43 | 12.60 | 25.04 | 1.44 | 0.36 | 0.11 | 0.30 | 2.20 |
| 33 | 16.27 ± 0.09 | — | — | — | 3.45 | — | — | — | 0.16 | — | — | — | 0.16 |

With reference to Table 7, the samples #28 to #33 are commercially available cosmetics in form of solution, gel, lotion, cream and mask and liquid medication. 0.1 mg of the samples are analyzed by the preferably embodiment of the invention and levels of paraben are recorded in Table 7. The results show that the samples #28 to #33 contain 0.13 to 2.20% of paraben, respectively. Accordingly, the preferably embodiment of the invention is suitable for monitoring level of paraben when the samples are merely 0.1 mg.

According to the results shown in Table 1 to 7, with respect to MP, EP, PP and BP, the method for monitoring level of paraben of the invention shows great linear relationship in a range between 0.1 to 10 μg/mL, wherein a coefficient of determination is $R^2 \geq 0.9995$ and a relative standard deviation is 9.86%. Moreover, the method for monitoring level of paraben of the invention is suitable for the sample in form of solution, gel, lotion, emulsion or cream.

As a result, by the derivatization reaction between sulfonyl chloride group of the derivatization reagent and hydroxyl group of paraben in the derivatization step "S2", the method for monitoring level of paraben of the invention has an improved recognition efficiency and specificity to paraben. Therefore, only 0.1 to 100 mg of the sample can be accurately analyzed. That is, the method for monitoring level of paraben of the invention is suitable to analyze the sample hard to obtain or expensive.

Moreover, via ionization of the tagged paraben to form the vaporized ion, followed by analyzing the mass-to-charge ratio of the vaporized ion by the analyzer in the analysis step "S4", thereby evaluating whether the sample contains paraben. That is, the method for monitoring level of paraben of the invention has a decreased time for detection and analysis, and is suitable for large-scale screening.

In addition, due to only a small amount of organic solvent is used in the pretreatment step "S1" and the extraction step "S3", the method for monitoring level of paraben of the invention produces decreased waste organic solvents, thereby preventing from environmental pollution.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for monitoring level of paraben in cosmetics comprising:

dissolving a sample in a solvent and obtaining a supernatant containing paraben by ultrasonic vibration and high speed centrifugation;

performing a derivatization reaction between a derivatization reagent and paraben by adding the derivatization reagent into the supernatant containing paraben to obtain a derivatization solution containing a tagged paraben;

extracting the derivatization solution containing the tagged paraben with an extractant to obtain an extract containing the tagged paraben;

co-crystallizing the extract containing the tagged paraben and α-cyanol-4-hydroxycinnamic acid (CHCA) as a matrix to form a co-crystallized extract-matrix mixture;

ionizing the co-crystallized extract-matrix mixture by a laser beam having a wavelength of 330 to 360 nm to form a vaporized ion; and analyzing mass-to-charge ratio of the vaporized ion with an analyzer to determine molecular weight thereof.

2. The method for monitoring level of paraben in cosmetics as claimed in claim 1, wherein the method further comprises adjusting temperature of the supernatant containing paraben to 30-80° C. prior to adding the derivatization reagent into the supernatant containing paraben.

3. The method for monitoring level of paraben in cosmetics as claimed in claim 1, wherein the derivatization reagent has a sulfonyl chloride group, wherein the derivatization reaction is performed with a hydroxyl group of paraben.

4. The method for monitoring level of paraben in cosmetics as claimed in claim 3, wherein the derivatization reagent is selected from 1,3-benzothiazole-6-sulfonyl chloride, 4-dimethylaminoazobenzene-4'-sulfonyl chloride or dansyl chloride.

5. The method for monitoring level of paraben in cosmetics as claimed in claim 1, wherein the sample is in a form of solution, lotion, emulsion, cream or gel.

6. The method for monitoring level of paraben in cosmetics as claimed in claim 1, wherein the method further comprises adding an internal standard into the supernatant containing paraben, and performing the derivatization reaction between the derivatization reagent and the internal standard.

7. The method for monitoring level of paraben in cosmetics as claimed in claim 6, wherein the internal standard is an isotope of paraben.

* * * * *